United States Patent
Brewer et al.

(10) Patent No.: US 8,205,917 B2
(45) Date of Patent: Jun. 26, 2012

(54) QUICK CONNECT FITTING FOR RESPIRATORY DEVICES

(75) Inventors: John Brewer, Marietta, GA (US);
Cassandra E. Morris, Roswell, GA (US); Joe Gordon, Mansfield, MA (US);
Stephen Gianelis, Abington, MA (US);
Dave Zitnick, Providence, RI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 846 days.

(21) Appl. No.: 12/334,123

(22) Filed: Dec. 12, 2008

(65) Prior Publication Data
US 2010/0147297 A1   Jun. 17, 2010

(51) Int. Cl.
*A47L 9/24*   (2006.01)
(52) U.S. Cl. .......................... 285/361; 285/7
(58) Field of Classification Search .................. 285/361, 285/396, 402
See application file for complete search history.

(56) References Cited

U.S. PATENT DOCUMENTS

| | | | | |
|---|---|---|---|---|
| 155,268 | A | * | 9/1874 | Stocker et al. ................ 285/361 |
| 2,500,955 | A | * | 3/1950 | Martinet et al. ................ 285/7 |
| 4,046,479 | A | | 9/1977 | Paley |
| 4,076,285 | A | | 2/1978 | Martinez |
| 4,569,344 | A | | 2/1986 | Palmer |
| 4,607,868 | A | | 8/1986 | Harvey et al. |
| 4,796,615 | A | | 1/1989 | Bullock et al. |
| 4,824,145 | A | | 4/1989 | Carlsson |
| 4,834,726 | A | | 5/1989 | Lambert |
| 5,071,413 | A | | 12/1991 | Utterberg |
| 5,116,088 | A | | 5/1992 | Bird |
| 5,357,946 | A | | 10/1994 | Kee et al. |
| 5,403,043 | A | | 4/1995 | Smet |
| 5,651,776 | A | | 7/1997 | Appling et al. |
| 5,707,086 | A | | 1/1998 | Treu et al. |
| 6,484,724 | B1 | | 11/2002 | Sloan |
| 6,609,520 | B1 | | 8/2003 | Carlsen et al. |
| 6,688,306 | B1 | | 2/2004 | Cise et al. |
| 7,191,782 | B2 | | 3/2007 | Madsen |
| 2006/0022465 | A1 | | 2/2006 | Yamauchi |
| 2006/0217683 | A1 | | 9/2006 | Patania |

FOREIGN PATENT DOCUMENTS

| | | |
|---|---|---|
| DE | 43 22 868 A1 | 1/1995 |
| GB | 569264 A | 5/1945 |
| WO | WO 2008/009645 A1 | 1/2008 |

* cited by examiner

Primary Examiner — Jerome W Donnelly
(74) Attorney, Agent, or Firm — James B. Robinson

(57) ABSTRACT

There is provided a novel fitting having male and female ends and a tapered internal luer-type seal. The male fitting end has a periphery upon which is mounted at least one boss. The female fitting end has a slot into which the boss may be inserted. At the bottom of the slot is a stop to limit the insertion depth of the boss. The male and female ends may then be rotated relative to each other to move the boss into a window on the female end. The window has a frame and the upper frame is angled slightly, corresponding to the boss, which serves to draw the male end farther in to the female end. The window has a side frame that stops the rotational movement of the boss. When the movement of the boss is stopped, the male and female tapers are in substantially leak-free contact. There is also provided a closed suction catheter using the novel fitting, such that the catheter may be easily and quickly removed and replaced.

2 Claims, 6 Drawing Sheets

QUICK CONNECT FITTING FOR RESPIRATORY DEVICES

BACKGROUND

A number of medical devices may be attached to the respiratory system of a patient while they are intubated with, for example, an endotracheal tube. Desirably, these devices may be attached, used for a period of time and detached for use elsewhere or for disposal. Various types of detachable fittings or connectors are currently in use, however, known fittings have a higher potential for failure than is desired due to manipulation by the user or caregiver.

A luer taper is used in a standardized system of small-scale fluid fittings used for making leak-free connections between a male-taper fitting and its mating female part on medical and laboratory instruments, including syringe tips, needles stopcocks and tubing. Luer taper fittings commonly have a 6 percent taper and may be tested according to (International Organization for Standardization) ISO 594-2. There are two common varieties of luer taper connections; Luer Lok® and Lure-Slip® fittings. Lure-Lok® fittings use a luer taper and are securely joined by means of a tabbed hub on the female fitting which engages threads in a sleeve on the male taper fitting. Luer-Slip® fittings conform to luer taper dimensions and are simply held together by friction. These luer fittings do not hold as well as would be desired and sometimes may be dislodged relatively easily and inadvertently by the patient or healthcare provider, resulting in the loss of ventilating system pressure and potential exposure of healthcare providers to communicable diseases of the patient. Luer fittings may also use standard threaded connections that entail screwing together two parts a number of turns to hold them securely but these fittings requires greater effort to connect and are not considered "quick connect" fittings.

Bayonet fittings are also well known and accepted in the medical field. Unfortunately, these fittings may be overridden in certain applications, like respiratory applications, resulting in a broken fitting and loss of ventilating system pressure.

Removing secretions from the tracheo-bronchial tree is an integral part of the care given to patients who are intubated and receiving mechanical or other artificial ventilation, for example. Secretions can be excessive in some respiratory disorders and constitute a serious threat to the patient having such respiratory disorders. The presence of an endotracheal tube and the associated sedation is a hindrance to the patient's efforts to clear secretions through natural coughing. In current medical practice, suction catheters are inserted through the endotracheal or tracheal tube into the trachea and main bronchus to clear such secretions from the patient's airway by suctioning.

Suctioning may be performed using an "open" or "closed" system. In the open system, the suction catheter is merely a flexible plastic tube that is inserted into the tracheal tube ventilating lumen with a source of suction connected to the proximal end of the suction catheter. The suction catheter is advanced as far as desired and suction is applied to remove secretions. Anything that the suction catheter touches before entering the lumen must be maintained in a sterile condition so a "sterile field" must be created on or next to the patient. The suction catheter must be carefully handled after it is used since it will be coated with the patient's secretions. In contrast, in the "closed" system, for example that disclosed in commonly owned U.S. Pat. No. 4,569,344, a device 10 which may be used to suction secretions uses a suction catheter 12 enclosed within a generally cylindrical plastic bag 14 to eliminate or minimize contamination of the suction catheter prior to use (FIG. 1). This is generally referred to as a "closed suction catheter" and is available under the trade name TRACH CARE® from BALLARD® Medical Products (Kimberly-Clark Corporation). As the patient requires artificial removal of secretions, the suction catheter 12 may be advanced through one end of the plastic bag 14, through a connecting fitting 1 6, into the tracheal tube and, if desired, into one of the main bronchi of the patient. The other, proximal end 17 of the suction catheter 12 is attached to a source of suction 19. Suction is applied to the proximal end 17 of the suction catheter 12 using a finger controlled valve 18 to remove the secretions. The other bronchus may likewise be aspirated. Secretions are thus drawn into the lumen of the suction catheter 12 and removed and the system remains closed. The suction catheter 12 is subsequently withdrawn from the tracheal tube and back into the plastic bag 14 to keep the circuit closed. Closed suction systems are generally preferred by healthcare providers since the provider is better protected from the patient's secretions. Closed suction systems are also easier and quicker to use since a sterile field need not be created each time the patient must be suctioned, as is required in open suction systems.

In order to change most current closed suction catheters, the patient must be disconnected from the system for a period of time while the ventilator is disconnected from the closed suction catheter that is to be replaced and connected to the new closed suction catheter. The new closed suction catheter is then connected to the endotracheal tube and ventilating of the patient is begun again. This procedure is obviously undesirable as it results in the patient being without mechanical breathing assistance for a period and it exposes the healthcare provider to the potentially communicable illnesses of the patient. Some closed suction catheter systems use detachable fittings like bayonet fittings, though, as mentioned above, these may have a higher potential for failure than is desired.

It would be desirable to have a fitting that is reliable and quick and easy to use. It would also be desirable to have a closed suction catheter that could be quickly and easily replaced without disconnecting the patient from the ventilating system.

SUMMARY

There is provided a novel fitting having male and female ends and a tapered internal luer-type seal. The male fitting end has a periphery upon which is mounted at least one boss. There may desirably be two bosses on the periphery of opposite sides of the male fitting end, and they may be of different lengths. The female fitting end has a slot into which the boss may be inserted. At the bottom of the slot is a stop to limit the insertion depth of the boss. The male and female ends may then be rotated relative to each other to move the boss into a window on the female end. The window has a frame and the upper frame is angled slightly which serves to draw the male end farther into the female end. The window has a side frame that stops the rotational movement of the boss. When the movement of the boss is stopped, the male and female tapers are in substantially leak-free contact.

There is also provided a closed suction catheter using the novel fitting, such that the catheter may be securely connected yet easily and quickly removed and replaced.

DETAILED DESCRIPTION

Reference is now made to the drawings wherein like numerals are used to designate like parts throughout.

Figure 1:
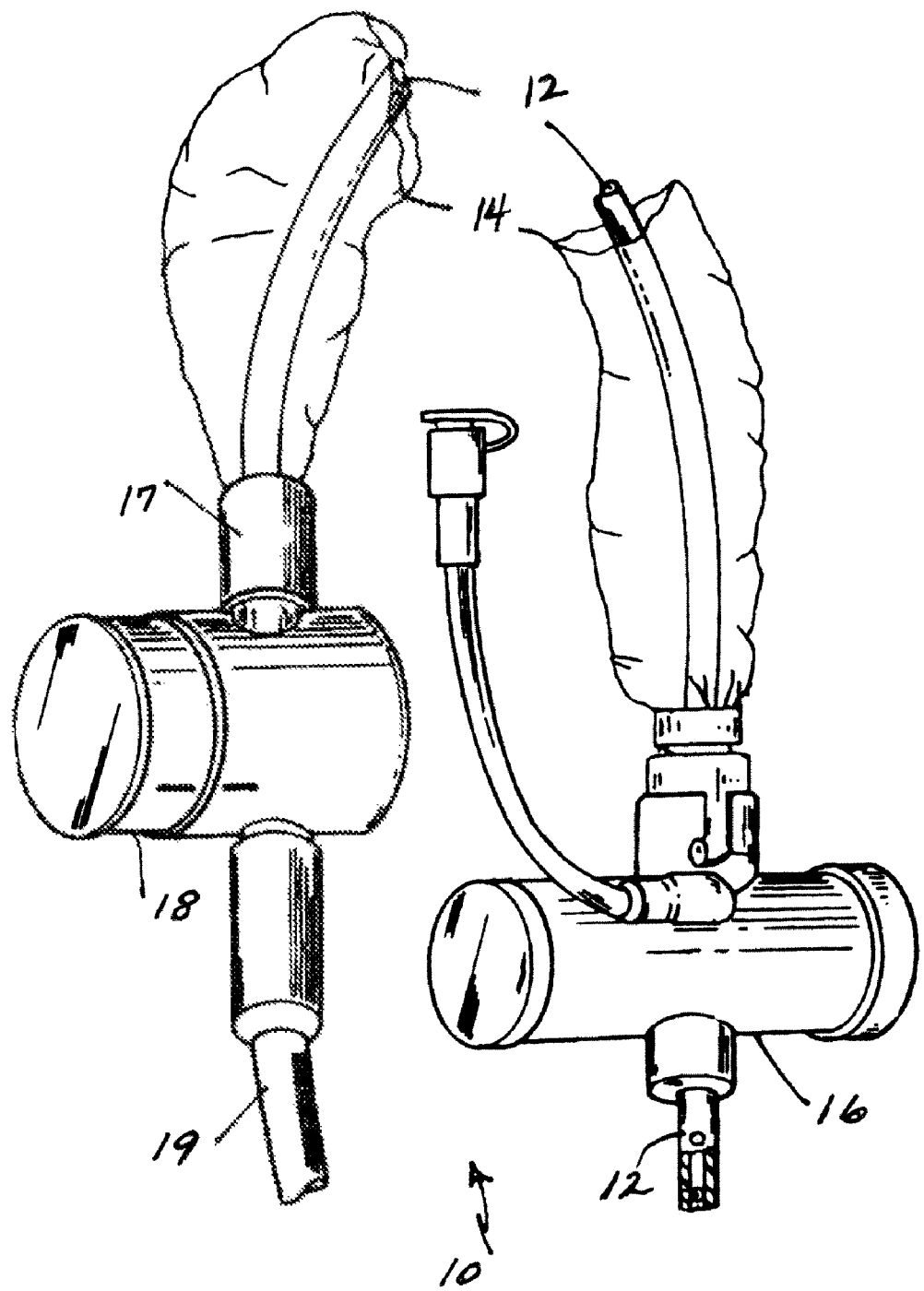
FIG. 1 shows a closed suction catheter device according to U.S. Pat. No. 4,569,344.

FIG. 1 illustrates an aspirating/ventilating apparatus disclosed U.S. Pat. No. 4,569,344, also referred to under the trade name TRACH CARE®. This closed suction catheter aspirating device 10 is attached to the patient's endotracheal tube using a fitting 16 and may be included as part of an overall ventilation circuit. The suction catheter 12 is enclosed within a plastic bag 14 to eliminate or minimize contamination of the catheter. As the patient requires artificial removal of secretions, the suction catheter is advanced through the fitting 16 of the ventilating device into the endotracheal tube (not shown), into the patient's airway and then into one of the bracheal tube of the patient. Suction is applied using a finger controlled valve 18 on the proximal end of the catheter 12 to remove the secretions. The closed suction aspirating device 10 of FIG. 1 may be used by attaching it directly to an endotracheal tube or in other configurations as long as it may move in a substantially straight alignment into the endotracheal tube. A more detailed description of this care device may be found in U.S. Pat. No. 4,569,344.

Figure 2:
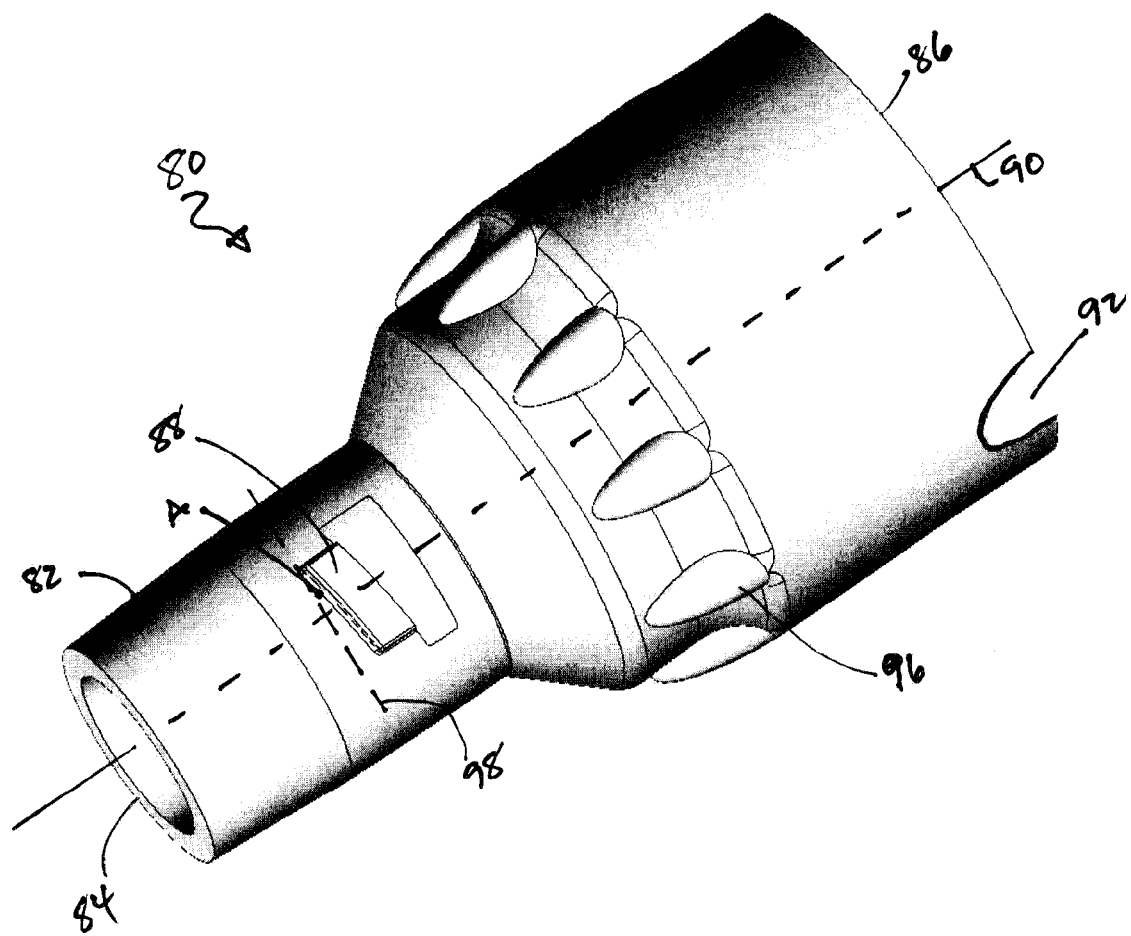
FIG. 2 is a drawing of the male fitting end of the novel quick connect fitting.

FIG. 2 is a drawing of the male fitting end 80 of the novel quick connect fitting. The male fitting end 80 tapers to a male luer taper 82 on its mating or distal end 84. On at least one side of the taper 82 is a tab or boss 88 that is used to engage a female counterpart pocket or slot. The boss 88 may be slightly angled relative to the perpendicular 98 of the centerline 90 of the male fitting end 80, indicated as angle "A", to assist it in securely mating with the female fitting end. Also visible on the proximal end 86 of the male fitting end 80 is an optional port 92 that may accommodate the irrigation line of a closed suction catheter (not shown) for example as well as optional grip dimples 96 to aid in gripping the piece with the hands.

Figure 3:
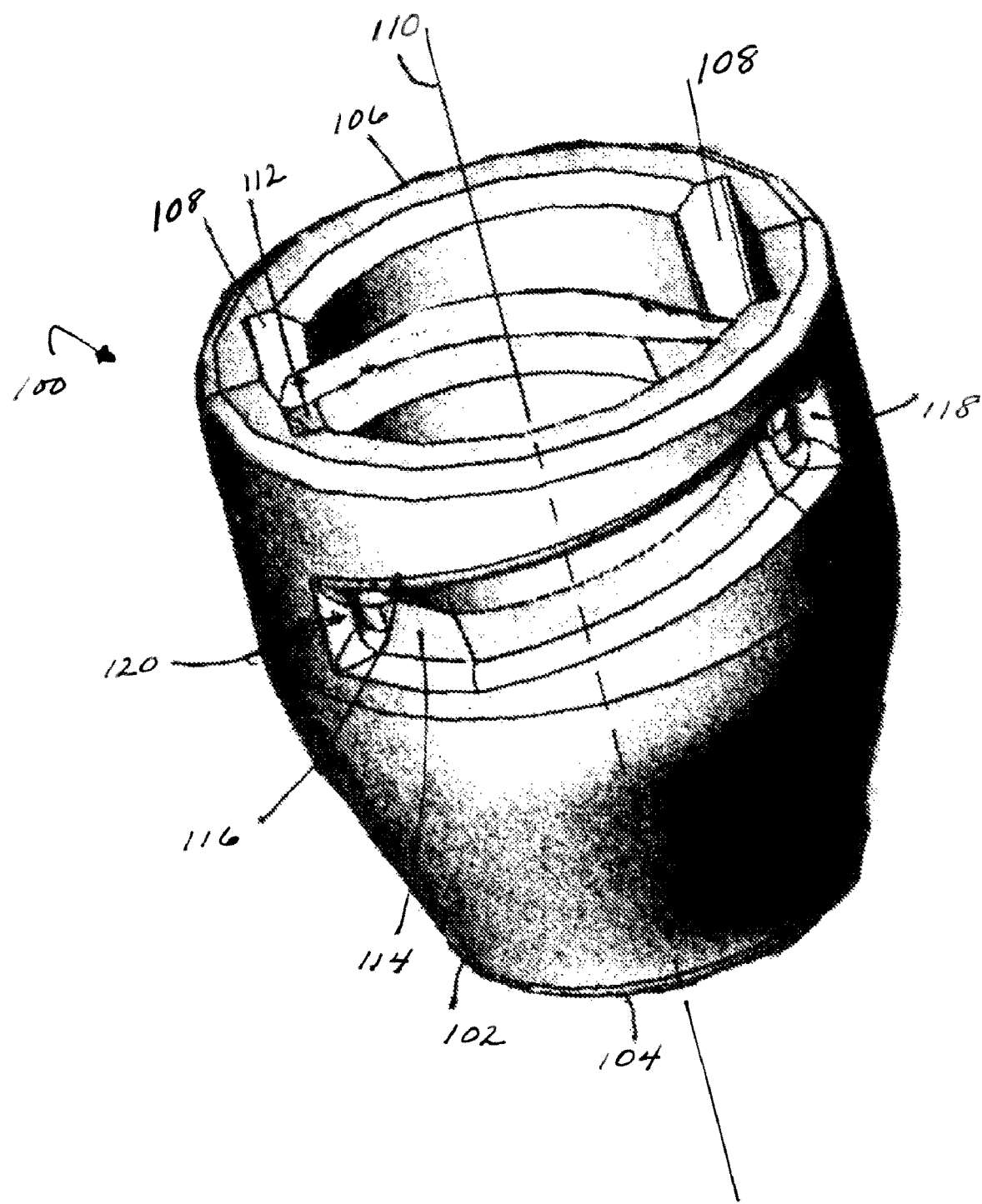
FIG. 3 is a drawing of the female fitting end of the novel quick connect fitting.

FIG. 3 is a drawing of the female fitting end 100 of the novel quick connect fitting. The female fitting end 100 has a pocket or slot 108 on either side of its proximal end 106 that is sized to allow insertion of the boss of the male fitting end. The female fitting end 100 has an auto-alignment stop 112 that is located at the bottom of each slot 108 to stop the movement of the male fitting end into the female fitting end 100. The female fitting end 100 further has a window 114 adjacent the slot 108, and in communication such that the male fitting end boss may be rotated into the window 114 once the boss is fully inserted and contacts the auto-alignment stop 112. The window 114 has a proximal side frame 116 that is desirably at the same angle as the boss relative to a perpendicular to the centerline 110 of the fitting. The window 114 has a near side frame 118 adjacent the stop that allows the boss to enter the window 114. The window 114 also has a far side frame 120 that stops the rotational movement of the boss. The female fitting end 100 has a female luer taper 102 located internally near the female fitting proximal end 106.

Figure 4:
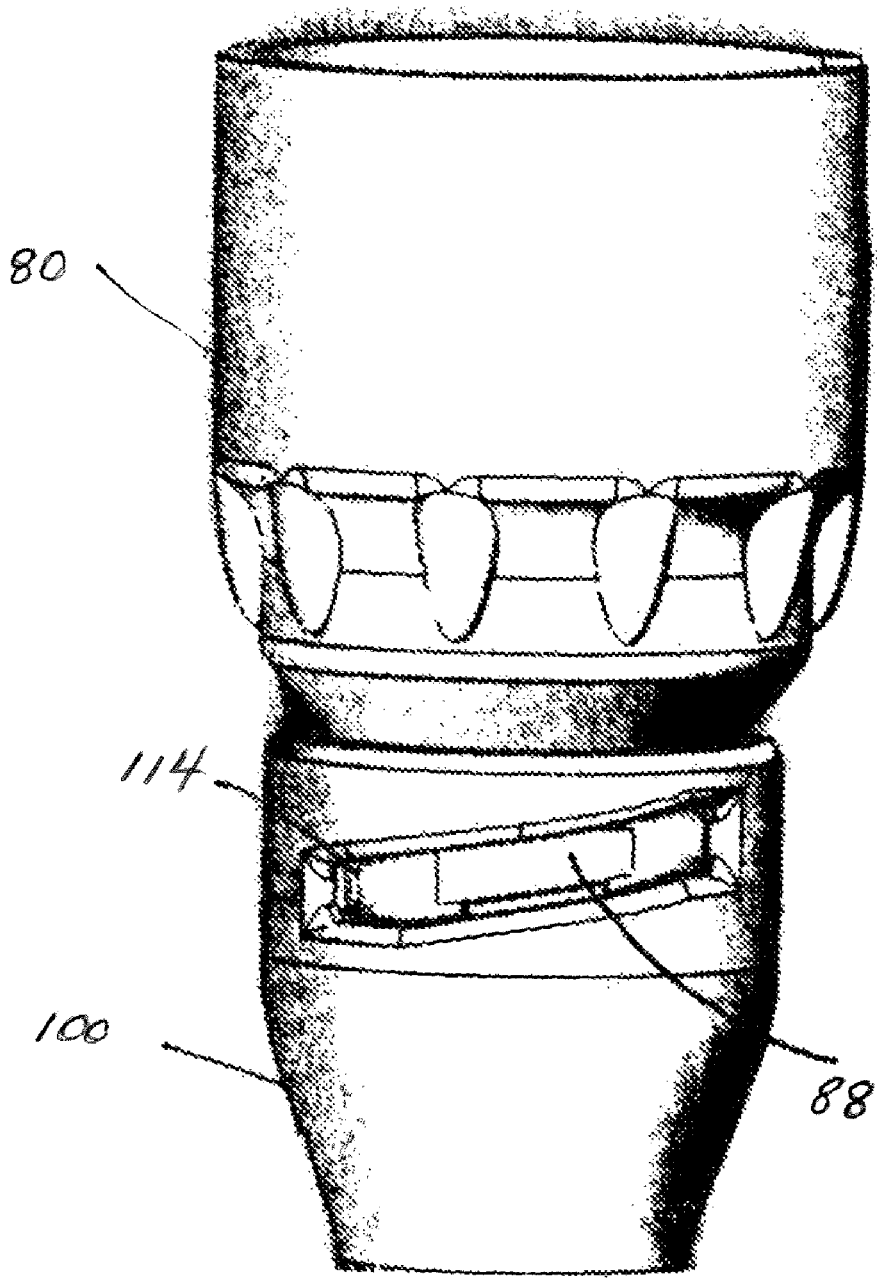
FIG. 4 shows the novel fitting described herein with the male portion on the right side and the female portion on the left side.

FIG. 4 is a drawing of the male fitting end 80 (distal end) engaged with the female fitting end 100 (proximal end). As can be seen, the boss 88 is within the window frame 114. The male luer taper 82 is resting against the inside of the female luer taper 102 (not visible).

The boss 88 on the male fitting end 80 may desirably be at an a downward angle of from 5 to 15 degrees relative to the perpendicular of the centerline 90 of the fitting to match the window 114 on the female fitting end 100. More desirably the angle may be between 7 and 12 degrees and still more desirably between 9 and 10 degrees. The male and female fitting ends may be rotated relative to each other in a right hand turn orientation to tighten them, desirably for about a quarter turn though more or less may be desirable in particular applications. A left hand turn orientation may also be used if desired.

In usage, once the boss of the male fitting end is inserted into the slot of the female fitting, it may advance only so far as to contact the stop at the bottom of the slot. The stop is placed at the proper depth so as to bring the luer tapers of the male and female fittings close together or into contact. Once the boss is fully inserted into the slot, the male fitting end may be rotated in only one direction relative to the female fitting to move the boss into position in the window. As the boss moves into the window, contact with the upper (angled) frame of the window causes the entire male fitting end to move slightly farther into the female fitting end. When the boss contacts the far window side frame movement is stopped and the tapers of the male fitting end and the female fitting end are fully engaged and are in substantially leak-free contact.

Should additional sealing capability be desired an O-ring type sealing system may be added to the novel fitting. In this embodiment an elastomeric O-ring may be placed over the luer taper of the male fitting end so that it will be compressed by the male and female fitting ends when they are fully engaged, and so improve the seal. Additional sealing and flexibility may also be added by making either the luer taper of the male fitting end or the female fitting end (or both) from an elastomeric material.

In still another embodiment, a surface treatment substance or texture may be added to either or both tapers to increase the seal created upon full engagement.

It should be appreciated that although the term "window" is used herein, it is not meant to imply that it comprises is a passageway from outside the fitting to inside the fitting, though for ease of manufacturing the open window is desirable. The window may be sealed from the outside (or closed) and only open toward the inside of the fitting so that the boss may rotate into the window.

It should also be noted that, though the drawings reference only two bosses on the male end there could be one, three or four if there were enough space on the periphery of the fitting and if this were desired for some reason. It should also be noted that the bosses could be of different widths and the slots could be of correspondingly different widths so that the male fitting could be inserted into the female fitting in only one orientation. Stated another way, if more than one boss were present, one boss could be longer than the other and only fit into one slot sized especially for that longer boss. There would then be only one position in which the male fitting could be inserted into the female fitting.

Figure 5:
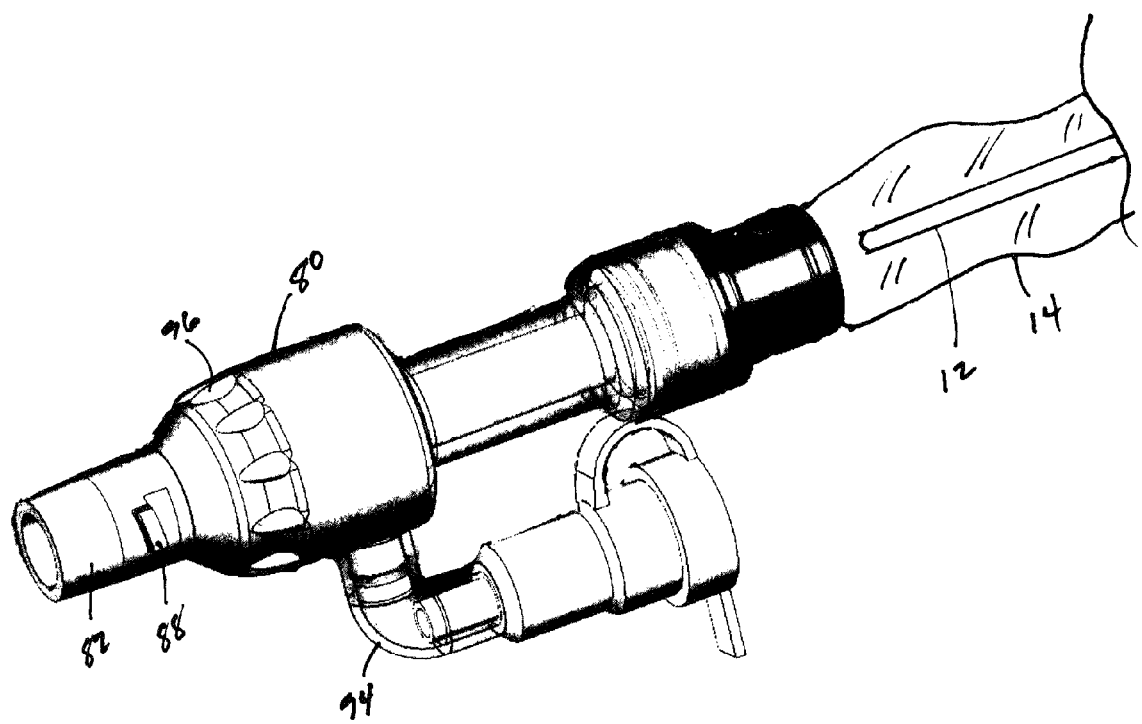
FIG. 5 is a drawing of the male fitting end having permanently attached thereto on its proximal end a closed suction catheter.
Figure 6:
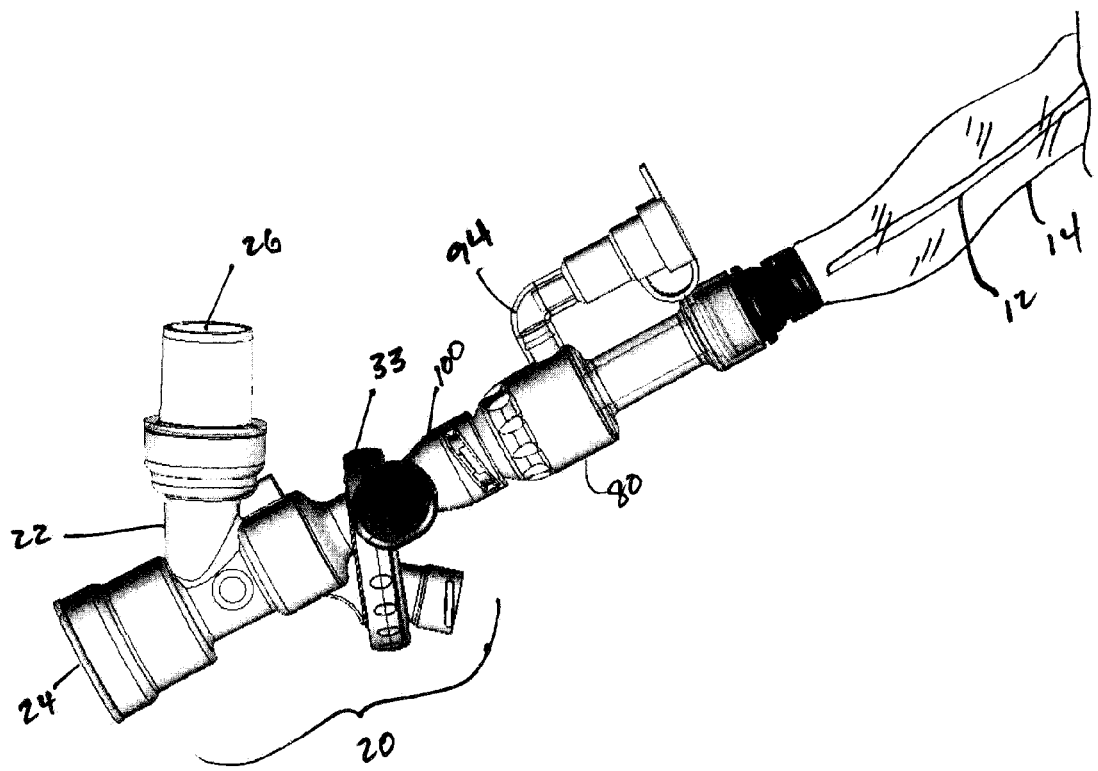
FIG. 6 is a drawing of the male fitting end having permanently attached thereto on its proximal end a closed suction catheter and where the male fitting end is releasably attached on its distal end to a female fitting end that is connected to a manifold.

The novel connector described can be used to connect a closed suction catheter to a ventilating circuit. Turning to FIG. 5, one can easily see that a closed suction catheter 12 in a plastic bag 14 may be permanently attached to, for example a male (or female) fitting end 80 described above on its proximal end. A number of other features of the male fitting end 80 are visible in this FIG. 5 including the grip dimples 96, boss 88, male luer taper 82 and the irrigation port 94. The mating fitting end may be permanently attached to the ventilating circuit. After a period of time or if the healthcare provider deems the catheter to need replacement, the male and female fittings may be quickly and easily disengaged and a new catheter attached. FIG. 6 is a drawing of the male fitting end 80 having permanently attached a closed suction catheter 12 in its plastic bag 14 on its proximal end and being releasably attached to a female fitting end 100 on its distal end. The female fitting end 100 is permanently attached to a respiratory manifold assembly 20. The assembly 20 may contain an elbow type connector 22, a rotating manifold 33, and ports 28, 30 and 32. The elbow 22 has a distal port 24 that connects to a tracheal tube and a proximal port 26 for connection to a mechanical ventilator.

The materials of construction of the novel connector may be conventional polymeric materials. A suitable polymer is available under the trade name LEXAN® polycarbonate. Other materials from which the connector may be made include polyethylene, polypropylene, acrylic, polyethylene terephthalate, polyurethane, nylon and styrene.

Modifications and variations of the presently disclosed device will be obvious to those of skill in the art from the foregoing detailed description. For example, though the discussion above mentions the quick connection of catheters, other devices such as cameras or other viewing devices may be connected to a ventilating system, provided they are of the appropriate size. The quick connection device described herein may also be used in applications other than respiratory care. Such modifications and variations are intended to come within the scope of the following claims.

I claim:

1. A quick connect fitting comprising a male fitting end having a body with a periphery upon which are two bosses of different sizes on opposite sides of said male fitting end, a female fitting end having slots corresponding with said bosses and into which said bosses may be advanced, a stop on said female fitting end to limit the insertion depth of said bosses into said slots, windows corresponding in size to their respective bosses into which the bosses may be rotatably moved from said slots to draw said male and female fitting ends closer together, and corresponding luer tapers on said male and female fitting ends.

2. A quick connect fitting comprising a male fitting end having a body with a periphery upon which is a boss, a female fitting end having a slot corresponding with said boss and into which said boss may be advanced, a stop on said female fitting end to limit the insertion depth of said boss into said slot, a window into which the boss may be rotatably moved from said slot to draw said male and female fitting ends closer together, and corresponding luer tapers on said male and female fitting ends, wherein said luer tapers are made from an elastomeric material.

* * * * *